United States Patent [19]

Kajikuri et al.

[11] Patent Number: 5,315,039
[45] Date of Patent: May 24, 1994

[54] METHOD FOR INHIBITING THERMAL DECOMPOSITION OF CYCLOALKANONE OXIMES

[75] Inventors: Hiroshi Kajikuri; Masaru Kitamura; Yasuhiko Higashio, all of Osaka, Japan

[73] Assignee: Sumitomo Chemical Company, Limited, Osaka, Japan

[21] Appl. No.: 981,472

[22] Filed: Nov. 25, 1992

[30] Foreign Application Priority Data

Jan. 10, 1992 [JP] Japan .................................. 4-002840

[51] Int. Cl.$^5$ ............................................ C07C 209/82
[52] U.S. Cl. ........................................ 564/2; 564/253
[58] Field of Search .......................... 564/2, 253, 254; 540/485

[56] References Cited

FOREIGN PATENT DOCUMENTS 1468022 2/1967 France .
47-41909 10/1972 Japan .
803375 10/1958 United Kingdom ................ 540/485

OTHER PUBLICATIONS

Armor, Journal of Catalysis, 70, 72-83 (1981).

Primary Examiner—Richard L. Raymond
Assistant Examiner—Shailendra Kumar
Attorney, Agent, or Firm—Cushman, Darby & Cushman

[57] ABSTRACT

Thermal decomposition of cycloalkanone oximes is inhibited by allowing nitrogen-containing compounds represented by the following formula (1) to coexist with the cycloalkanone oximes:

$$NR_1R_2R_3 \qquad (1)$$

(wherein $R_1$, $R_2$ and $R_3$ each represents a hydrogen atom or a lower alkyl group).

9 Claims, No Drawings

METHOD FOR INHIBITING THERMAL DECOMPOSITION OF CYCLOALKANONE OXIMES

The present invention relates to a method for inhibiting thermal decomposition of cycloalkanone oximes.

Thermal decomposition of cycloalkanone oximes occurs when they are used at high temperatures, for example, when they are vaporized for use. Not only this thermal decomposition causes loss of cycloalkanone oximes, but also the decomposition products are sometimes harmful for the subsequent operations. Accordingly, a problem is how to inhibit the thermal decomposition.

A method is proposed wherein at least one substance selected from alkali metals or alkaline earth metals per se and oxides, hydroxides and alcoholates thereof is allowed to be present in a vaporizing zone of, for example, cyclohexanone oxime (Japanese Patent Kokoku No. 47-41909). However, the method is not satisfactory yet, since it does not sufficiently inhibit the thermal decomposition of cycloalkanone oximes.

The inventors have conducted intensive research on thermal stability of cycloalkanone oximes and have found that the thermal decomposition can be easily and efficiently inhibited by allowing specific compounds to coexist with cycloalkanone oximes. As a result, the present invention has been accomplished.

According to the present invention, thermal decomposition of cycloalkanone oximes is inhibited, by allowing nitrogen-containing compounds represented by the following formula (1) to coexist with cycloalkanone oximes:

$$NR_1R_2R_3 \quad (1)$$

(wherein $R_1$, $R_2$ and $R_3$ each represents a hydrogen atom or a lower alkyl group).

The present invention will be explained in detail below.

The cycloalkanone oximes in the present invention are not limitative. Examples are cycloalkanone oximes of 5-10 carbon atoms such as cyclopentanone oxime, cyclohexanone oxime, cycloheptanone oxime, cyclooctanone oxime, cyclononanone oxime and cyclodecanone oxime.

As the compounds which inhibit the thermal decomposition of cycloalkanone oximes in coexistence therewith, there may be used nitrogen-containing compounds represented by the following formula (1):

$$NR_1R_2R_3 \quad (1)$$

(wherein $R_1$, $R_2$ and $R_3$ each represents a hydrogen atom or a lower alkyl group).

As examples of the nitrogen-containing compounds, mention may be made of ammonia and lower alkylamines of 1-12 total carbon atoms such as monomethylamine, dimethylamine, trimethylamine, monoethylamine, diethylamine, triethylamine, monopropylamine, dipropylamine, tripropylamine, monobutylamine, dibutylamine, tributylamine, ethylmethylamine and dimethylethylamine. These may be used each alone or a mixture of two or more.

Amount of the nitrogen-containing compounds may be 0.01 mole % or more, usually 0.1-200 mole % based on the cycloalkanone oxime.

The nitrogen-containing compounds are used in any manners. For example, when cycloalkanone oximes are fed at a high temperature, the nitrogen-containing compounds may be previously mixed with the cycloalkanone oximes. Alternatively, the nitrogen-containing compounds are fed separately from cyclohexanone oximes so that they all are well mixed immediately after feeding. The cycloalkanone oxime may be used in the form of a mixture with organic solvents such as an alcohol, benzene or toluene.

The nitrogen-containing compounds used are repeatedly used after they are separated and recovered from mixtures with cycloalkanone oximes and others.

Although thermal decomposition of cycloalkanone oximes is easily and efficiently inhibited by allowing specific nitrogen-containing compounds to be present, this effect is especially displayed in a process of vaporization of the cycloalkanone oximes. Temperature of the vaporizing zone in this case varies depending on cycloalkanone oximes, but is usually 160° C. or higher under atmospheric pressures. The temperature may be lower under reduced pressure.

The present invention will be explained by the following nonlimiting examples.

EXAMPLE 1

A quartz tube (10 mm inner diameter, 40 cm long) was inserted in an electric furnace set at 350° C. A solution containing cyclohexanone oxime (43.5% by weight) in methanol was fed into the quartz tube at a rate of 6.9 g/hr in order to vaporize the cyclohexanone oxime. A nitrogen gas containing ammonia (5% by volume) was fed at a rate of 4.2 l/hr as a carrier gas. Amount of ammonia was about 35 mole % based on cyclohexanone oxime. After this operation was continued for 256 hours, feeding of the cyclohexanone oxime solution was discontinued. The quartz tube was cooled in a nitrogen gas atmosphere and then weight of carbonaceous materials deposited on the wall of the quartz tube was 26.6 mg.

COMPARATIVE EXAMPLE 1

Example 1 was repeated except that nitrogen gas (4.2 l/hr) was used as a carrier gas in place of the nitrogen gas containing ammonia. Carbonaceous materials (225.5 mg) were deposited on the wall of the quartz tube.

EXAMPLE 2

In a stainless steel sealed vessel (50 ml internal volume) were charged cyclohexanone oxime (1 g) and one drop of 5.6 wt % aqueous ammonia (0.03 g), and the atmosphere therein was replaced with nitrogen gas. The vessel was heated in an oven set at 180° C. for 1 hour. Amount of ammonia was 1 mole % based on cyclohexanone oxime. After the vessel was cooled, the residue in the vessel was analyzed by gas chromatography. Amount of residual cyclohexanone oxime was 93% by weight against the charged amount.

COMPARATIVE EXAMPLE 2

Example 2 was repeated except that one drop of 16.7 wt % aqueous potassium hydroxide solution (0.03 g) was added in place of the aqueous ammonia. Amount of potassium hydroxide was 1 mole % based on the cyclohexanone oxime. Amount of residual cyclohexanone oxime was 85% by weight against the charged amount.

COMPARATIVE EXAMPLE 3

Example 2 was repeated except that no aqueous ammonia was added. Amount of residual cyclohexanone oxime was 82% by weight against the charged amount.

EXAMPLE 3

Example 2 was repeated except that one drop of 29.8 wt % aqueous triethylamine solution (0.03 g) was added in place of the aqueous ammonia. Amount of triethylamine was 1 mole % based on the cyclohexanone oxime. Amount of residual cyclohexanone oxime was 92% by weight against the charged amount.

What is claimed is:

1. A method for inhibiting thermal decomposition of cycloalkanone oximes which comprises allowing nitrogen-containing compounds represented by the following formula (1) to coexist with cycloalkanone oximes:

$$NR_1R_2R_3 \quad (1)$$

wherein $R_1$, $R_2$ and $R_3$ each represents a hydrogen atom or a lower alkyl group.

2. A method according to claim 1, wherein the cycloalkanone oximes have 5-10 carbon atoms.

3. A method according to claim 2, wherein the cycloalkanone oxime having 5-10 carbon atoms is cyclohexanone oxime.

4. A method according to claim 1, wherein the nitrogen-containing compound is ammonia.

5. A method according to claim 1, wherein the nitrogen-containing compounds are lower alkylamines having totally 1-12 carbon atoms.

6. A method according to claim 5, wherein the lower alkylamine having totally 1-12 carbon atoms is at least one member selected from trimethylamine and triethylamine.

7. A method according to claim 1, wherein amount of the nitrogen-containing compound is 0.01 mole % or more based on the cycloalkanone oxime.

8. A method according to claim 1, wherein the cycloalkanone oxime is in the form of a mixture with organic solvents.

9. A method according to claim 8, wherein the organic solvent is alcohol, benzene or toluene.

* * * * *